United States Patent
Krogmann

(10) Patent No.: US 10,082,479 B2
(45) Date of Patent: Sep. 25, 2018

(54) METHOD FOR PRODUCING A PH HALF-CELL, AND A PH HALF-CELL

(71) Applicant: Innovative Sensor Technology IST AG, Ebnat-Kappel (CH)

(72) Inventor: Florian Krogmann, Kreuzlingen (CH)

(73) Assignee: INNOVATIVE SENSOR TECHNOLOGY IST IG, Ebnat-Kappel (CH)

( * ) Notice: Subject to any disclaimer, the term of this patent is extended or adjusted under 35 U.S.C. 154(b) by 49 days.

(21) Appl. No.: 15/303,264

(22) PCT Filed: Mar. 30, 2015

(86) PCT No.: PCT/EP2015/056829
§ 371 (c)(1),
(2) Date: Oct. 11, 2016

(87) PCT Pub. No.: WO2015/158533
PCT Pub. Date: Oct. 22, 2015

(65) Prior Publication Data
US 2017/0168008 A1    Jun. 15, 2017

(30) Foreign Application Priority Data
Apr. 17, 2014 (DE) .................. 10 2014 105 575

(51) Int. Cl.
*G01N 27/31* (2006.01)
*G01N 27/36* (2006.01)
(Continued)

(52) U.S. Cl.
CPC .......... *G01N 27/36* (2013.01); *G01N 27/302* (2013.01); *G01N 27/333* (2013.01); *C23C 14/24* (2013.01);
(Continued)

(58) Field of Classification Search
CPC ............................ G01N 27/302; G01N 27/36
See application file for complete search history.

(56) References Cited

U.S. PATENT DOCUMENTS

| 4,883,563 A | 11/1989 | Kotani |
| 5,384,031 A | 1/1995 | Anderson |
| 9,279,781 B2 | 3/2016 | Wilhelm |

FOREIGN PATENT DOCUMENTS

| DE | 3134760 A1 | 9/1982 |
| DE | 19714474 A1 | 10/1998 |

(Continued)

OTHER PUBLICATIONS

EPO computer-generated English language translation of Vonau et al. DE 19714474 A1 Downloaded Jan. 23, 2018.*
(Continued)

*Primary Examiner* — Alexander Stephan Noguerola
(74) *Attorney, Agent, or Firm* — Bacon & Thomas, PLLC

(57) ABSTRACT

A method for producing a pH half-cell by means of which, in combination with a reference electrode and an evaluation electronics unit, a pH value of a medium can be determined, comprises the following steps: applying a first structure and a second structure to a substrate, wherein the first structure is applied by means of a thin-film method and forms a resistance element having a temperature-dependent resistance value, and wherein the second structure can be employed to derive a pH-dependent potential; applying a structured passivation glass layer, wherein the passivation glass layer substantially covers the first structure and leaves the second structure substantially uncovered; applying a mixed-conducting glass, wherein the mixed-conducting glass is substantially applied to the region that was left uncovered by the passivation glass layer; and applying a
(Continued)

pH-sensitive glass, wherein the pH-sensitive glass is applied to the mixed-conducting glass.

17 Claims, 2 Drawing Sheets

(51) Int. Cl.
G01N 27/333 (2006.01)
G01N 27/30 (2006.01)
C23C 14/34 (2006.01)
C23C 14/24 (2006.01)
C23C 16/44 (2006.01)
C23C 16/06 (2006.01)

(52) U.S. Cl.
CPC .......... *C23C 14/3407* (2013.01); *C23C 16/06* (2013.01); *C23C 16/44* (2013.01)

(56) References Cited

FOREIGN PATENT DOCUMENTS

| | | |
|---|---|---|
| DE | 29923433 U1 | 1/2001 |
| DE | 102007016197 A1 | 10/2008 |
| DE | 102010054019 A1 | 6/2012 |
| DE | 102012101254 A1 | 8/2013 |
| DE | 102014105575 A1 | 10/2015 |
| EP | 0269031 A2 | 6/1988 |
| EP | 0673506 B1 | 9/1995 |
| GB | 2015742 A | 9/1979 |

OTHER PUBLICATIONS

German Search Report, German Patent Office, Munich, DE, dated Mar. 16, 2015.
International Search Report, EPO, The Netherlands, dated Jun. 9, 2015.
English Translation of the International Preliminary Report on Patentability, WIPO, Geneva, CH, dated Oct. 27, 2016.

* cited by examiner

METHOD FOR PRODUCING A PH HALF-CELL, AND A PH HALF-CELL

TECHNICAL FIELD

The invention relates to a method for producing a pH half-cell by means of which a pH value of a medium can be determined, as well as such a pH half-cell.

BACKGROUND DISCUSSION

The qualitative determination of the pH value of a medium is an essential process parameter in many processes. Various techniques for determining the pH value are therefore known from the prior art.

Typically, ion-selective electrodes are used to measure ion activity. The most common variant is apparently a glass electrode. Glass electrodes are normally understood to be solid-state membranes consisting of siliceous glasses, which are usually melted from oxides or carbonates and then changed to the final version by glassblowing. If such a glass electrode is dipped into an aqueous solution, a hydrated film forms on the pH value-sensitive membrane glass. This is also done on the inner side of the glass membrane, which is in contact with a specific buffer solution such as a potassium chloride buffer (PCL). A reference electrode is also needed in addition to the glass electrode, so that the pH value can be measured.

The design of such glass electrodes is generally very large. For this reason, the possible integration density, i.e., the number of other sensors per unit area, is very restricted, and is therefore also not suitable for use in processes with very small amounts of the analytes, such as in the nL, µL, or mL range. Furthermore, the problem with such glass electrodes is that they may not be used in many applications, due to their fragility and the possibility of contamination in the event that the glass breaks.

From the prior art, ion-selective field effect transistors (ISFETs) are known that measure the pH value with a pH-sensitive film (such as $Ta_2O_5$, SiN, and $Al_2O_3$) which is applied to the gate. With such ISFETs, the potential to be measured is converted to a current signal.

The disadvantage of ISFETs is that they react very sensitively to radiation. Particularly when used in biological processes, sterilization is essential, and recourse is frequently made to gamma sterilization. This is not feasible with ISFET sensors. Furthermore, ISFETS are generally produced in CMOS (complementary metal-oxide semicoductor) processes, since the electronics unit for evaluation is applied directly to the chip. This limits a potential integration of other measured variables, since significant incompatibilities exist between the processes. Accordingly, at high temperatures, many metals cannot be used at all, or only sparingly.

Likewise, thick-film electrodes based upon $RuO_2$ or other metal oxides with a pH value sensitivity are known from the prior art, which typically work by means of a metallic fixed lead.

The disadvantage of thick-film electrodes is generally the strong dependence of the measuring signal upon the redox potential of the analyte. For this reason, such thick-film electrodes are of interest only in areas of use where the redox potential of the analyte remains basically constant.

Likewise, thick-film sensors are known from the prior art. These work on the basis of a pH-sensitive glass that is measured by means of a fixed lead (made of platinum, for example). High-temperature co-fired ceramics (HTCC for short) are used as a substrate for the thick-film sensors.

The use of HTCC processes limits the possible materials and structured precision, due to the shrinkage during the HTCC process, as well as the compatibilities of the materials with each other. Due to the reproducibility of the shrinkage while baking, these sensors are kept relatively large. Furthermore, all materials involved must withstand very high temperatures.

In addition to a high-temperature, multilayer ceramic as a substrate, steel substrates are also used. The use of steel substrates is associated with the disadvantage that they either oxidize while baking the thick-film paste, which can cause contamination of the sensitive layers, or baking must occur in a low oxygen atmosphere, which, in turn, cannot be done with many materials, or is incompatible with them.

Furthermore, dye sensors are known from the prior art that change their color or fluorescence times, depending upon the pH value. These are read out by an optical system.

The disadvantage in this context is that the dye sensors must be read out by very complex optical systems. In addition, they frequently have low long-term stability. Furthermore, they frequently require recalibration after sterilization processes. Since the quality of the connection of the optical system plays a role in the measuring precision, frequently, at least a one-point calibration must be performed in disposable applications (i.e., single use products). Another disadvantage that such dye sensors have is a relatively low long-term stability. In the final analysis, this makes the sensor expensive to use. Furthermore, dye sensors degrade very quickly—for example, by bleaching.

SUMMARY OF THE INVENTION

The object of the invention is, therefore, to overcome the aforementioned problems.

The object is achieved with a method for producing a pH half-cell, a pH half-cell, and a sensor system for determining a pH value.

With regard to the method, the object is achieved with a method for producing a pH half-cell, wherein, by means of the pH half-cell, in combination with a reference electrode and an evaluation electronics unit, a pH value of a medium can be determined, wherein the method for producing the pH half-cell has the following steps:

Applying a first structure and a second structure to a substrate, wherein the first structure is applied by means of a thin-film method and forms a resistor element having a temperature-dependent resistance value, and wherein the second structure can be employed to derive a pH-dependent potential;

Applying a structured passivation glass layer, wherein the passivation glass layer substantially covers the first structure and leaves the second structure substantially uncovered;

Applying a mixed-conducting glass, wherein the mixed-conducting glass is mainly applied to the region that was left uncovered by the passivation glass layer; and Applying a pH-sensitive glass, wherein the pH-sensitive glass is applied to the mixed-conducting glass.

According to the invention, a pH half-cell is proposed which is produced by the combination of thin-film processes and thick-film processes, wherein the pH half-cell is constructed in a purely passive manner, i.e., without integrated electronics.

By means of thin-film processes, structures or film thicknesses can be produced in a range of 50 nm to 1 µm.

Conventional methods are sputtering, evaporation deposition, or chemical vapor deposition (CVD for short).

By comparison, structures or thick-film layer thicknesses of approximately 2 μm and more can be created by means of thick-film processes. Conventional methods are screen printing, stencil printing, or dipping methods, and possibly inkjet methods as well. Through the combination, the advantages of thin-film technology (small structural sizes, many different film systems that are economical to use) and thick-film technology (effective passivation films, robustness in relation to process fluctuations, large variety of materials for mixed materials (glasses, glass/metal mixed layers)) can be combined. Furthermore, by combining the two methods for producing a pH half-cell, it is also possible to measure other physical and/or chemical variables such as the temperature, the redox potential, ion concentration (such as Cl), dissolved oxygen, flow speed, or the overall organic carbon, in addition to merely measuring the pH value of the medium. For this purpose, only another structure, e.g., of platinum, needs to be applied to the substrate of the pH half-cell.

In the following, a "mixed-conducting glass" is understood to be a glass that conducts both electrons and ions. A "pH-sensitive glass" is to be understood as a glass that reacts with moisture or water and forms a very thin, invisible, water-containing hydrated layer on the surface. This gel or hydrated layer is pH value-selective and interacts with the hydrogen ions of the measuring solution. The hydrated layer can be considered a selective barrier, wherein the hydrogen ions are able to pass through, yet all other ions can pass through only to a substantially restricted extent.

In one advantageous embodiment, the second structure is applied by means of a thin-film method, wherein, especially, a sputtering, evaporation deposition, or chemical gas phase deposition method is used as the thin-film method.

In another advantageous embodiment, the structured passivation glass layer, the mixed-conducting glass, and the pH-sensitive glass are applied by means of a thick-film method, wherein, especially, a screen printing, a stencil printing, or a dipping or inkjet method is used as the thick-film method.

In another advantageous embodiment, the material from which the first structure is formed has platinum or doped platinum.

In another advantageous embodiment, the material from which the second structure is formed has platinum, doped platinum, or gold. The embodiment especially provides that, in the event that the second structure is formed from platinum or doped platinum, a gold film is applied to the second structure formed from platinum or doped platinum, such that the gold film substantially covers the second structure formed from platinum or doped platinum, the mixed-conducting glass substantially covers the gold film, and the pH-sensitive glass substantially covers the mixed-conducting glass.

In another advantageous embodiment, the method includes a trimming step in which the first structure is trimmed to a given resistance value under reference conditions after the first structure is applied. Such reference conditions are described or specified in standard DIN 60751 from 2008.

In another advantageous embodiment, the first structure is configured such that it has at least two connecting contacts by means of which the resistor element is electrically connected to the evaluation electronics unit, and the second structure is configured such that it has at least one additional connecting contact which enables the discharge of the pH-dependent potential to the evaluation electronics unit.

With regard to the pH half-cell, the object is achieved with a pH half-cell which, especially, can be produced according to one or more of the preceding embodiments, wherein the pH half-cell has at least:
a substrate,
a first structure formed on the substrate and a second structure, wherein the first structure forms a resistor element with a temperature-dependent resistance value, and the second structure can be used to discharge a pH-dependent potential, wherein the first and the second structures have a maximum film thickness of 2 μm,
a structured passivation glass layer, which substantially covers the first structure and leaves the second structure substantially uncovered,
a mixed-conducting glass that is applied in the region left substantially uncovered by the passivation glass layer, wherein the mixed-conducting glass has a first glass layer thickness of not less than 2 μm,
a pH-sensitive glass that is applied to the mixed-conducting glass, wherein the pH-sensitive glass has a second glass layer thickness of not less than 2 μm.

In one advantageous embodiment, a material serves as the substrate that has an expansion coefficient of at least $9 \cdot 10^{-6}$ $K^{-1}$. For example, the use of zirconium oxide ($ZrO_2$) as a substrate has proven to be advantageous.

In another advantageous embodiment, the first structure has platinum or doped platinum, and the second structure has platinum, doped platinum, or gold. In the event that the second structure is formed from gold, the pH half-cell additionally has an adhesive film, e.g., of Cr or TiW, between the substrate and second structure consisting of gold. The embodiment especially provides that, in the event that the second structure has platinum or doped platinum, a gold film is provided that substantially covers the second structure having platinum or doped platinum, such that the gold film substantially covers the second structure having platinum or doped platinum, the mixed-conducting glass substantially covers the gold film, and the pH-sensitive glass substantially covers the mixed-conducting glass.

In another advantageous embodiment, the second structure is formed such that it has a substantially circular base surface, and the passivation glass layer has a substantially circular opening.

In another advantageous embodiment, the first structure has two connecting contacts, by means of which the resistance of the resistor element of the first structure can be determined, and the second structure has a connecting contact, by means of which the pH-dependent potential can be discharged.

In another advantageous embodiment, the passivation glass layer has a passivation glass layer thickness of not less than 2 μm.

With regard to the sensor system, the object is achieved with a sensor system for determining a pH value of the medium with a pH half-cell, which, especially, can be produced according to one of the above-described embodiments, a reference electrode, and an evaluation electronics unit.

In one advantageous embodiment of the sensor system, the reference electrode needed to determine the pH value is realized on a surface of the substrate of the pH half-cell.

BRIEF DESCRIPTION OF THE DRAWINGS

The invention is explained in more detail based upon the following drawings. Illustrated are.

DETAILED DISCUSSION IN CONJUNCTION WITH THE DRAWINGS

Figure 1:
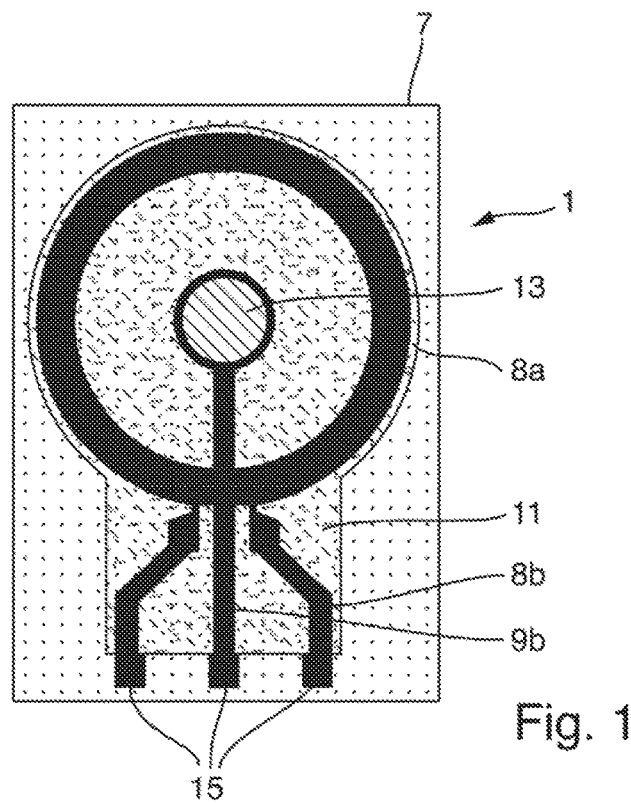
FIG. 1: is an embodiment of the pH half-cell according to the invention, which is completely processed.

FIG. 1 shows an embodiment of the pH half-cell according to the invention. The pH half-cell has a substrate 7 on which a platinum film 6 is applied by means of thin-film processes.

The substrate 7 preferably consists of a material that has an expansion coefficient of at least $9 \cdot 10^{-6}$ $K^{-1}$. In this context, materials based upon zirconium oxide ($ZrO_2$), such as partially or fully stabilized $ZrO_2$, have proven to be particularly suitable substrate materials. Other materials that have a similar expansion coefficient are also conceivable as well. By using a material that has a corresponding expansion coefficient, the expansion coefficient is adapted to the expansion coefficient of the glasses located on substrate 7, and thermally induced stress or strain is reduced.

A first structure 8 and a second structure 9 consisting of the platinum film 6 are formed on the substrate 7. The first structure 8 forms a resistor element 8a with a temperature-dependent resistance value. Typically, platinum, doped platinum, or, also, gold is used as the material for producing the first structure 8. The resistor element is preferably designed as a Pt100 or Pt1000 resistor element and should accordingly possess a target resistance of 100 Ohm or 1000 Ohm. To achieve such a resistance value, the resistor element 8a is designed in a meandering form. Since the resistance value cannot be precisely "adjusted" when applying the first structure 8, the first structure 8 is typically brought or trimmed to a predefined resistance value according to DIN standard 60751 from 2008, by means of a trimming process. Typically, this is carried out by means of laser trimming, wherein the change in the resistance value arises by means of laser beam-induced changes in the material. In order to be able to determine the resistance value of the resistor element of the first structure 8, the first structure 8 has two lines 8b and two connecting contacts 15, by means of which the pH half-cell 1 can be connected to an external evaluation electronics unit 3.

In addition to the first structure 8, a second structure 9 is also applied to the substrate 7. The second structure 9 serves to discharge a pH-dependent potential. For this purpose, the second structure 9 that is formed substantially in the middle of the substrate 7 has an electrode surface 9a that is connected to a connecting contact 15 by means of a line 9b. The connecting contact 15 in turn serves to connect the second structure 9 to the external, i.e., separately constructed, evaluation electronics unit 3.

As depicted in FIG. 1, the connecting contacts 15 are formed at the edge of the substrates 7, so as to be easily connectable from there to the evaluation electronics unit 3. An alternative to this are vias through the substrate 7, by means of which the pH half-cell 1 can be connected at the rear of the substrate 7. This is especially advantageous for integrating the pH half-cell 1 in an assembly.

As already mentioned, the second structure 9 is arranged substantially in the middle on the substrate 7. The electrode surface 9a of the second structure 9 is preferably formed to be circular. A structured passivation glass layer 11 is applied to the substrate 7 with the first structure 8 and the second structure 9. This is structured so that it has a circular opening 19 in the region of the electrode surface 9a, so that other is needed films can be introduced or applied in this opening 19. Due to the circular design of the electrode surface 9a, and thereby the circular opening 19, in the passivation glass layer 11, it is possible to reduce the internal stress in the passivation glass layer 11, especially at the edge area of the opening 19. With a different geometric design of the openings 19—especially, designs that have edges or the like—it was revealed that crack formation occurs to a greater extent at the edges.

The first structure 8 is arranged—for example, circularly—around the second structure 9. A different geometry of the first structure 8 is, however, also conceivable, such as a rectangular design of the meandering resistor element 8a.

The first and the second structures 8, 9 are ideally applied to the substrate 7 in a single thin-film processing step. Of course, in this case, the material from which the first structure 8 and the second structure 9 are formed is one and the same. Platinum has proven to be particularly useful in this context, since it is very chemically inert and accordingly offers fewer restrictions in the selection of the process, and also offers the possibility of using high temperature processes (processes that must be carried out at temperatures greater than 800° C.) while further processing the pH half-cell. Furthermore, platinum can also be in direct contact with the measuring solution, without corrosive effects. For example, another structure that serves to measure another physical and/or chemical variable, such as the redox potential, can be formed from platinum. The first and second structures 8, 9 that are typically applied together by thin-film technology have a maximum height of about 2 μm.

It is of course also conceivable to make the first structure 8 and the second structure 9 different from each other, and hence to also use different materials and to achieve different heights of the two structures.

As already mentioned, a structured passivation glass layer 11, which is applied by means of a thick-film method in a thick-film processing step, is located on the first and second structures 8, 9. The passivation glass layer 11 has a minimum passivation glass layer thickness of 2 μm, wherein a maximum passivation glass layer thickness of about 100 μm is possible, due to the thick-film technology. The passivation glass layer 11 is designed such that it has an essentially circular opening 19, so that the base surface of the electrode surface 9a of the second structure 9, which is also substantially circular, is accessible for other processing steps. FIG. 1 shows the completely processed pH half-cell 1, whereas FIG. 2 shows a pH half-cell in which only the first and second structures 8, 9, as well as the passivation glass layer 11, are applied to the substrate 7.

Figure 2:
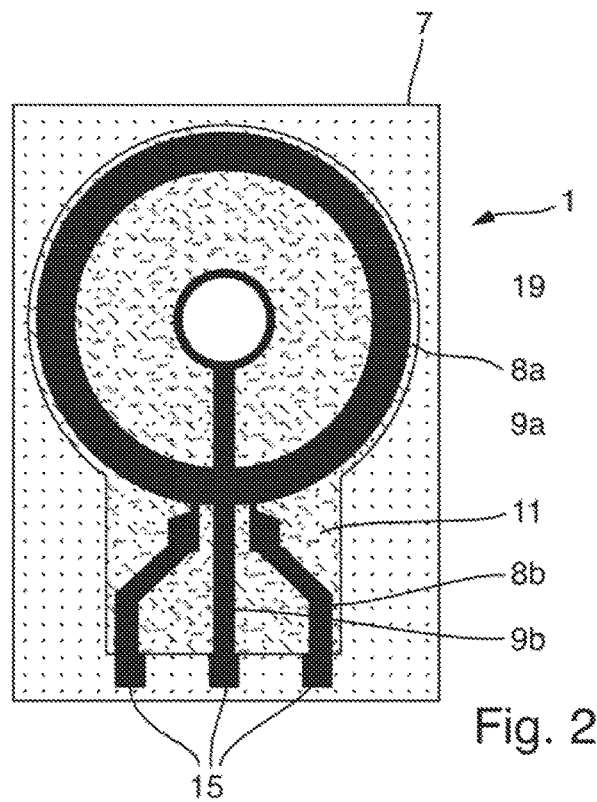
FIG. 2: is an incompletely processed pH half-cell.

In FIG. 2, the electrode surface 9a is indicated with light gray, to show that the base surface of the electrode surface 9a of the second structure 9 is still free, despite the already applied passivation glass layer 11, and other layers can accordingly be applied to this surface. In contrast, the line 9b of the second structure 9 is depicted as black, to emphasize that this line is covered by the passivation glass layer 11.

Figure 3:
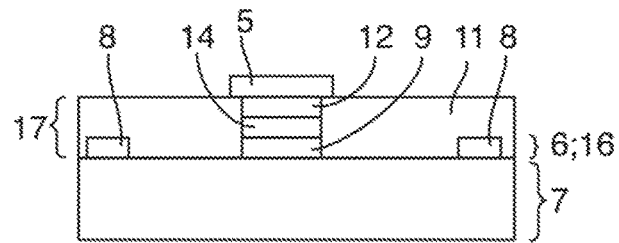
FIG. 3: is a cross-section of the pH half-cell according to the invention.

FIG. 3 shows a cross-section of the pH half-cell 1 according to the invention, by means of which the further layout of the pH half-cell 1 according to the invention is described. The first and the second structures 8, 9, as well as the passivation glass layer 11, are configured in FIG. 3 according to the description of FIG. 1 and FIG. 2. Based upon this layout, the pH half-cell 1 has a gold film 14 that substantially covers the electrode surface 9a of the second structure 9. This gold surface 14 is typically applied using thick-film methods. Alternatively, the gold film can also be applied using thin-film methods. The application of the gold film 14 is necessary only when the second structure 9 is formed from platinum or doped platinum. It is also conceivable to directly form the second structure 9 from a gold film 14 on the substrate 7. However, this is associated with increased effort in terms of production, such that it is generally easier to first apply the second structure 9 of platinum or doped platinum, and then the gold film 14, to the second structure 9.

A mixed-conducting glass 12 is on the second gold film 14 that is mainly applied in the region free of the passivation glass layer 11, i.e., the circular opening 19. It is also conceivable for the mixed-conducting glass 12 to not only fill the opening, but also to at least partially cover the passivation glass layer 11 as well.

The mixed-conducting glass 12 is applied using a thick-film method and has a first glass layer thickness of at least 2 μm. The mixed-conducting glass can be up to about 100 μm thick at a maximum.

A pH-sensitive glass 13 is then applied to the mixed-conducting glass 12. This pH-sensitive glass 13 is then applied by means of one of the known thick-film methods.

As can easily be seen in FIG. 3, the second structure 9—especially, the electrode surface 9a of the second structure 9—the mixed-conducting glass 12, as well as the gold film 14, are surrounded by the passivation glass layer 11 and the pH-sensitive glass 13, so that contact with the medium 5 is excluded or prevented.

Figure 4:
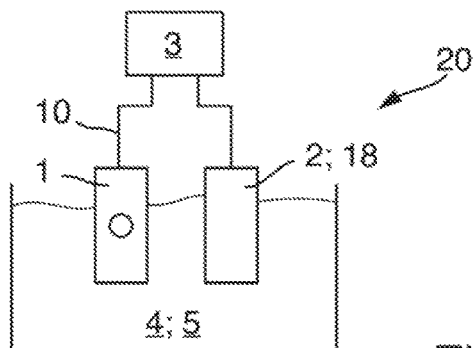
FIG. 4: is a sensor system for determining the pH value.

FIG. 4 shows a sensor system 20 for determining the pH value 4 of the medium 5, wherein the sensor system 20 comprises a pH half-cell 1 which is designed according to the description of FIGS. 1 through 3, a reference electrode 2, and an evaluation electronics unit. The pH half-cell 1 is connected to the evaluation electronics unit 3 by the three connecting contacts 15, which accordingly discharge the pH-dependent potential to determine, on the one hand, the pH value 4 of the medium 5 and, on the other hand, to measure the resistance value of the resistor element 8a of the first structure 8, in order to determine the temperature of the medium 5 therefrom. Such a sensor system 20 is accordingly able to simultaneously or in parallel determine the pH value 4 and the temperature of the medium 5. As already mentioned, it is possible with a suitable design of the pH is half-cell 1 to also measure other, or possibly additional, variables, such as the redox potential, in addition to the temperature as a measured variable.

To determine the pH value 4, the evaluation electronics unit 3 requires a reference electrode 2 or a reference half-cell. This reference electrode 2 can, for example, be a reference electrode 2 designed separately from the pH half-cell 1 and known from the prior art. Given the combination of the two production methods, i.e., thick-film and thin-film technology, the possibility also exists, however, of forming an internal reference electrode on the pH half-cell 1 and using it to evaluate the pH value 4. Depending upon the application, however, this is not always necessary, such that, for example, a reference signal is available from an ion-sensitive sensor, or that a silver/silver chloride (Ag/AgCl—) pseudo-reference (i.e., a reference electrode without a diaphragm and KCl buffer solution) or a pure platinum reference can be resorted to, given the knowledge of the processes.

Figure 5:
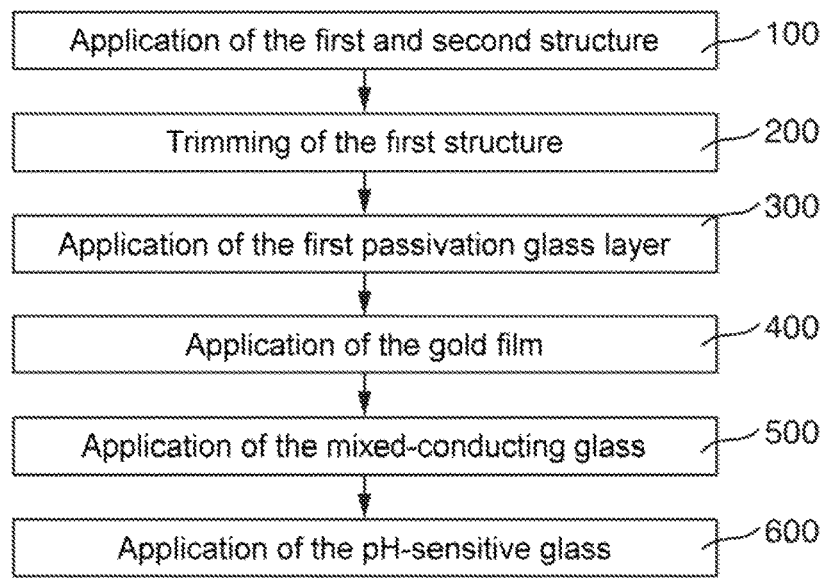
FIG. 5: is the progression of the method according to the invention for producing a pH half-cell.

FIG. 5 shows an example of the method sequence according to the invention for producing a pH half-cell 1. In this context, the first structure 8 and the second structure 9 are applied in a first step 100 using a thin-film method such as sputtering, evaporation deposition, or chemical gas phase deposition. In a second step 200, the meandering resistor element 8a of the first structure 8 is trimmed to a set resistance value under reference conditions. In a third step 300, the structured passivation glass layer 11 is applied using a thick-film method such as screen printing, stencil printing, or dipping or inkjet methods. In a fourth step 400, the gold film 14 is applied by means of a thick-film method. As already mentioned, the second structure 9 can already be formed of gold, such that the additional application of the gold film 14 is unnecessary in this case. In a fifth step 500, the glass layer 12 is applied by means of a thick-film method. Finally, the pH-sensitive glass 13 is applied in a sixth step 600.

The invention claimed is:

1. A method for producing a pH half-cell by means of which, in combination with a reference electrode and an evaluation electronics unit, a pH value of a medium can be determined, wherein the method for producing the pH half-cell has the following steps:
    applying a first structure and a second structure to a substrate, wherein the first structure is applied by means of a thin-film method and forms a resistor element having a temperature-dependent resistance value, and wherein the second structure can be employed to derive a pH-dependent potential;
    applying a structured passivation glass layer, wherein the passivation glass layer substantially covers the first structure and leaves the second structure substantially uncovered;
    applying a mixed-conducting glass, wherein the mixed-conducting glass is mainly applied to the region that was left uncovered by the passivation glass layer; and
    applying a pH-sensitive glass, wherein the pH-sensitive glass is applied to the mixed-conducting glass.

2. The method according to claim 1, wherein:
the second structure is applied by means of a thin-film method; and
a sputtering, evaporation deposition, or chemical gas phase deposition method is used as the thin-film method.

3. The method according to claim 1, wherein:
the structured passivation glass layer, the mixed-conducting glass, and the pH-sensitive glass are applied by means of a thick-film method.

4. The method according to claim 1, wherein:
the material from which the first structure is formed has platinum or doped platinum.

5. The method according to claim 1, wherein:
the material from which the second structure is formed has platinum, doped platinum, or gold.

6. The method according to claim 5, wherein:
in the event that the second structure is formed from platinum or doped platinum, a gold film is applied to the second structure formed from platinum or doped platinum, such that the gold film substantially covers the second structure formed from platinum or doped platinum, the mixed-conducting glass substantially covers the gold film, and the pH-sensitive glass substantially covers the mixed-conducting glass.

7. The method according to claim 1, further having:
a trimming step, in which the first structure is trimmed to a given resistance value under reference conditions, after the first structure is applied.

8. The method according to claim 1, wherein:
the first structure is configured such that it has at least two connecting contacts, by means of which the resistor element is electrically connected to the evaluation electronics unit, and the second structure is configured such that it has at least one connecting contact, which enables the discharge of the pH-dependent potential to the evaluation electronics unit.

9. A pH half-cell which is produced according to claim 1, having at least:
a substrate;
a first structure formed on the substrate and a second structure, wherein said first structure forms a resistor element with a temperature-dependent resistance value, and said second structure can be used to discharge a pH value-dependent potential, and wherein said first and the second structures have a maximum film thickness of 2 μm;
a structured passivation glass layer that substantially covers said first structure and leaves said second structure substantially free;
a mixed-conducting glass that is applied in a region substantially left uncovered by said structured passivation glass layer, wherein said mixed-conducting glass has a first glass layer thickness of not less than 2 μm; and
a pH-sensitive glass that is applied to said mixed-conducting glass, wherein said pH-sensitive glass has a second glass layer thickness of not less than 2 μm.

10. The pH half-cell according to claim 9, wherein:
a material serves as said substrate that has an expansion coefficient of at least $9 \cdot 10^{-6}$ $K^{-1}$.

11. The pH half-cell according to claim 9, wherein:
said first structure has platinum or doped platinum, and said second structure has platinum, doped platinum, or gold.

12. The pH half-cell according to claim 11, wherein:
in the event that said second structure has platinum or doped platinum, a gold film is provided that substantially covers said second structure having platinum or doped platinum, such that said gold film substantially covers said second structure having platinum or doped platinum, said mixed-conducting glass substantially covers said gold film, and said pH-sensitive glass substantially covers said mixed-conducting glass.

13. The pH half-cell according to claim 9, wherein:
said second structure is formed such that it has a substantially circular base surface, and said structured passivation glass layer has a substantially circular opening.

14. The pH half-cell according to claim 9, wherein:
said first structure has two connecting contacts, by means of which the resistance of the resistor element of said first structure can be determined, and said second structure has a connecting contact, by means of which the pH-dependent potential can be discharged.

15. The pH half-cell according to claim 9, wherein:
said structured passivation glass layer has a passivation glass layer thickness of not less than 2 μm.

16. A sensor system for determining a pH value of a medium with a pH half-cell, according to claim 9;
a reference electrode; and
an evaluation electronics unit.

17. The sensor system according to claim 16, wherein:
said reference electrode is realized on a surface of said substrate of said pH half-cell.

\* \* \* \* \*